United States Patent [19]

Stamos

[11] Patent Number: 5,533,504
[45] Date of Patent: Jul. 9, 1996

[54] APPARATUS FOR CONTROLLING AIR FLOW THROUGH NASAL PASSAGES

[76] Inventor: Louis Stamos, 506 Wafer Dr., Tarpon Springs, Fla. 34689

[21] Appl. No.: 304,931

[22] Filed: Sep. 13, 1994

[51] Int. Cl.⁶ .................................................. A62B 9/06
[52] U.S. Cl. .............................. 128/201.18; 128/200.24; 128/201.27
[58] Field of Search ................... 128/200.24, 200.26, 128/201.18, 201.23, 201.26, 201.27, 202.27, 204.12, 207.14, 207.15, 207.16, 207.17, 207.18, 911

[56] References Cited

U.S. PATENT DOCUMENTS

| | | |
|---|---|---|
| 598,467 | 2/1898 | Carence . |
| 690,663 | 1/1902 | Pratt .................................. 128/201.27 |
| 1,978,994 | 10/1934 | Fortunato .......................... 128/201.16 |
| 2,015,617 | 9/1935 | Claudius ............................. 128/201.18 |
| 2,064,986 | 12/1936 | Mezz . |
| 2,681,652 | 1/1953 | Laxton . |
| 2,757,665 | 8/1956 | Tanikawa . |
| 3,266,490 | 8/1966 | Klinger et al. .................... 128/201.27 |
| 4,077,068 | 3/1978 | Anderson ........................... 128/201.27 |
| 4,090,511 | 5/1978 | Gray .................................... 128/201.27 |
| 4,280,493 | 7/1981 | Council . |
| 4,676,240 | 6/1987 | Gardy ................................. 128/207.14 |
| 4,944,310 | 7/1990 | Sullivan . |

FOREIGN PATENT DOCUMENTS

| | | |
|---|---|---|
| A5043 | 12/1905 | France . |
| A6006 | 8/1906 | France . |
| 76055 | 11/1893 | Germany . |
| 6743 | of 1904 | United Kingdom . |
| 2086733 | 5/1982 | United Kingdom . |

Primary Examiner—Edgar S. Burr
Assistant Examiner—William J. Deane, Jr.
Attorney, Agent, or Firm—James Creighton Wray

[57] ABSTRACT

Apparatus for controlling air flow through nasal passages having a frame with first and second plates for positioning on a face along opposite sides of a nose. The plates have first and second extensions extending forwardly and inwardly and contacting a face of the user beneath the nose and above an upper lip. Rods extend inward from the plates, and nose-engaging pads are mounted on inward proximal ends of the rods. A strap connects the plates and extends rearwardly around a head of a user. The strap has first and second sections with hook and loop complementary fasteners for adjusting the strap to fit a head of a user, and holding the strap. The extensions have a curved bar which slides within a curved channel for adjusting the position between the plates. A threaded clamp has an enlarged head mounted in an elongated recess at the rear of the channel, and has a shaft which extends through an elongated opening in the channel and through an opening in the extension which slides within the channel. A fastener nut is threaded on an outer end of the fastener shaft to clamp the extensions in a selected position. Inward facing surfaces of the plates have cushions along the rear edge and bottom edge portions, and the channel extension has cushions along the edges for contacting the user's face. The plates have multiple threaded openings in which the threaded rods may be selectively received.

18 Claims, 1 Drawing Sheet

U.S. Patent         Jul. 9, 1996         5,533,504
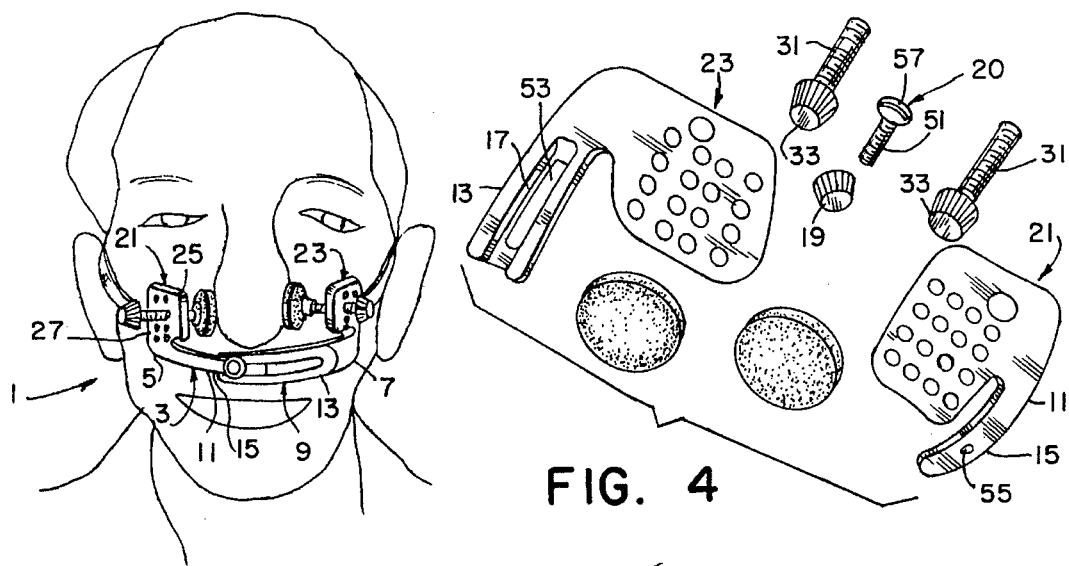
FIG. 1
FIG. 4
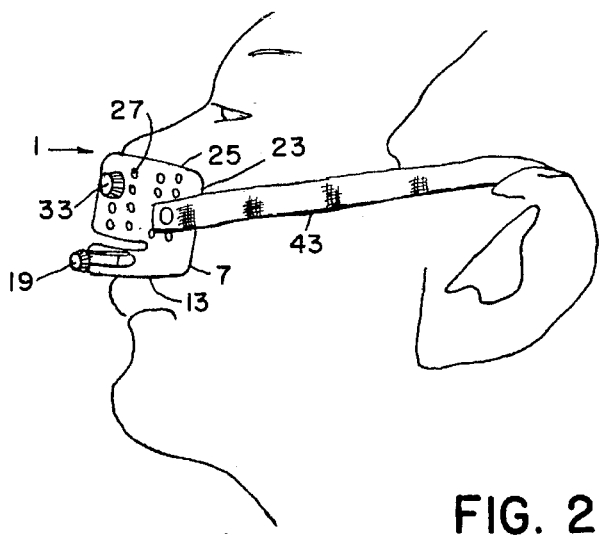
FIG. 2
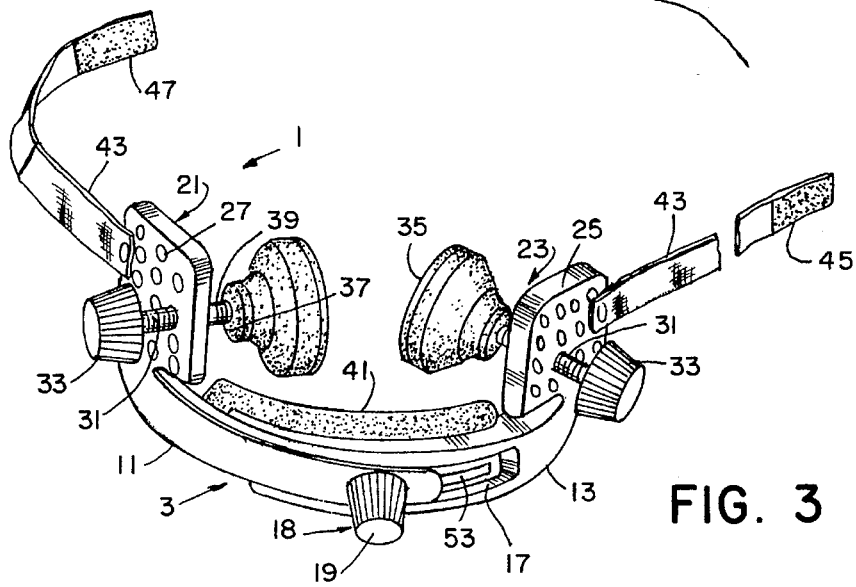
FIG. 3

APPARATUS FOR CONTROLLING AIR FLOW THROUGH NASAL PASSAGES

BACKGROUND OF THE INVENTION

The present invention is directed to solving a problem of producing noise while sleeping.

Snoring has been described as vibrations of soft tissue in and adjacent the breathing passages, and particularly vibrations of the uvula and soft palate during regular or irregular breathing at night.

The vibrations are believed to be caused by the regular or irregular flow of air across opposite surfaces of the soft tissue, which causes the soft tissue to vibrate and to establish variations in compressive patterns within the air chambers and passages in the body, thus producing amplified sound much like a vibrating reed and hollow channel produce amplified sounds in wind instruments and organ pipes.

The vibrations produced may not be injurious to the vibrated soft tissue or to the air passages in a human body. However, the sound so produced may be of substantial volume and may be disquieting to others. Procedures have been devised for avoiding snoring, such as surgical intervention by removing a portion or portions of the uvula, or by altering the uvula to redirect flow. Other devices have been provided to maintain patency of airways. Complex airway connecting system have been proposed.

Needs exist for non-invasive devices which reduce or prevent snoring and/or the sounds emanating from a snorer.

One of the problems that must be considered is that devices which reduce or prevent snoring must be sufficiently non-obtrusive so as to avoid interfering with sleep, and particularly with the REM sleep or deep sleep, which is beneficial.

Persons have differently shaped bone and cartilage structures, different shapes and thickness of soft tissue, and different facial and nasal surfaces, providing problems in mounting external devices.

A need has existed for non invasive snoring preventors.

SUMMARY OF THE INVENTION

The present invention is a device for prevention or reduction of snoring.

The present invention overcomes problems associated with snoring by adjusting, fine tuning and controlling air flow through nasal passages.

The present invention provides the control with lightweight soft devices which do not interfere with sleep. The control is provided with devices which may comfortably narrow, close or restrict enlargement or openings of nasal passages. The devices have multiple mounting structures to provide adjustment for comfort and effectiveness. The devices of the present invention have the ability to selectively close or to selectively permit opening of portions of the nasal passages to alter the breathing patterns which may promote snoring.

The device has two plates with cushion pads inside. A connecting rod has its upper ends connected to the lower ends of the plates. Each cushion pad has a knob on the outside of the plate to adjust the pressure of the pad against the nostril. The plates are connected to an elastic band to be worn around the head. The device is to be worn during the night. Adjusting the pressure of the pads against the nostril with the side knobs will make one stop snoring.

The stop snoring device is attached to the nose with a knob at each nostril. The knobs are independently adjusted to restrict the flow of air into each nostril. The device is worn at night, and as a person begins to snore an adjustment to the knob will stop the person from snoring. How much to adjust the device is determined by each person (i.e. restricting the left nostril only can be effective for that person). Not only can the device stop snoring, when the knobs are completely closed the device can be used for diving.

This invention provides a combination anti-snoring and diving device. The diving device is useful by turning the nose pads all of the way in so that they completely close the nose passage. When the device is used to prevent or reduce snoring, the nose pads may be moved slightly outward so they restrict the full opening of the nasal passages.

A snoring preventor and diving device has a frame with first and second plates for positioning on a face along opposite sides of a nose. The plates have first and second extensions extending forwardly and inwardly and contacting a face of the user beneath the nose and above an upper lip. Rods extend inward from the plates, and nose-engaging pads are mounted on inward proximal ends of the rods. A strap connects the plates and extends rearwardly around a head of a user. The strap has first and second sections with hook and loop complementary fasteners for adjusting the strap to fit a head of a user, and holding the strap. The extensions have a curved bar which slides within a curved channel for adjusting the position between the plates. A threaded clamp has an enlarged head mounted in an elongated recess at the rear of the channel, and has a shaft which extends through an elongated opening in the channel and through an opening in the extension which slides within the channel. A fastener nut is threaded on an outer end of the fastener to clamp the extensions in a selected position.

Inward facing surfaces of the plates have cushions along the rear edge and bottom edge portions, and the channel extension has cushions along the edges for contacting the user's face. The plates have multiple threaded openings in which the threaded rods may be selectively received. A threaded bushing connected to the nose pad holder is unscrewed from an inner distal end of a rod. The rod is unscrewed from the threaded opening in the plate using the knob at the distal end of the rod. The rod is screwed into another threaded opening in the plate, and the threaded bushing on the pad holder is screwed onto the inner proximal end of the rod. The device is ready to be used to prevent snoring or to permit diving. In the diving modification, the knobs turn the rods inward to tightly compress sides of the nose to close the nasal passageways. In the snoring mode, the pads are turned inward against surfaces of the nose until the nasal passageway is restricted sufficiently to prevent vibrations of the uvula and soft palate.

An anti-snoring and diving apparatus has a frame with first and second side plates. First and second central extensions extend respectively from the first and second side plate. The first and second extensions have slides for relatively sliding the extensions, and a clamp is connected to the extensions for clamping the extensions in a selected inner relationship of the slides. First and second rods are respectively mounted in the first and second plates. The first and second rods have respective first and second proximal ends extending inward from the plates toward each other. First and second nose-engaging pads are connected to the rods for engaging and compressing sides of a nose with the pads, and a strap is connected to the plates for holding the plates on the face of a user.

The plates have cushions spaced from the nose-engaging pads for resting against a face of a user. The cushions are located along an inner face of the plates and along rearward and lower edges of the inner face. Cushions are located on one of the extensions for engaging a facial area of a user above an upper lip of the user and beneath a nose of the user.

The slides have a curved outward opening channel formed in a first inner extension connected to a first plate. The second extension is formed as a curved bar for sliding in the outward facing channel. The extension cushions are mounted around a rearward facing portion of the forward opening channel.

An elongated opening extends along the base of the channel and a recess in a rear face of the first extension. The second extension has a hole extending through the extension. The clamp has a fastener extending through the hole with a head of the fastener in the recess. The clamp also has a clamping nut engaging the fastener in front of the second extension.

The first and second plates have multiple openings for receiving the rods.

The multiple openings are threaded and the rods have complementary threads. The rods have knobs fixed on outer ends thereof for turning the rods and the pads connected to the proximal ends of the rods inward and outward according to the turning of the rods in the holes. The multiple holes comprise precise positioning of the rods for precise positioning of the pads on sides of the nose of the user.

The pads have threaded bushings for receiving proximal ends of the threaded rods and for mounting the pads on the threaded proximal ends of the rods for removing the pads from the proximal ends and turning the rods out of the holes for repositioning the rods in other holes before re-securing the threaded the bushings and pads to proximal ends of the rods for correctly aligning the pads with surfaces of the nose of the user.

The strap has first and second strap sections. The first strap section is connected to the first plate which has an outward facing hook-type fastener strip. The second strap is fastened to the second plate and has an inward facing loop-type fastener strip complementary to the hook-type fastener strip at an outer end.

These and further and other objects and features of the invention are apparent in the disclosure, which includes the above and ongoing written specification, with the claims and the drawings.

BRIEF DESCRIPTION OF THE DRAWINGS

FIG. 1 is a front elevation of the device being worn.

FIG. 2 is a side elevation of the device being worn.

FIG. 3 is a perspective view of the device.

FIG. 4 shows elements of the device.

DETAILED DESCRIPTION OF THE PREFERRED EMBODIMENTS

Referring to FIG. 1, an anti-snoring and diving device is generally indicated by the numeral 1. A frame 3 has a first, left side plate 5 and a second, right side plate 7, as seen from the perspective of a user. The sides are joined by an adjustable cross-member 9, which has extensions 11 and 13 rigidly connected to the opposite side plates. The extension 11 comprises a curved bar 15, which slides in a complementary curved outward facing channel 17 in extension 13. The curved bar 15 and the channel 17 are slides.

A clamp 18 has a knob 19 with threads for receiving a threaded shaft of a screw fastener 20, the head 57 of which is held in a recess behind the elongated channel 17. The clamp shaft of fastener 20 extends through an opening in the curved bar to fix the relationship of the bar and channel.

The halves 5 and 7 respectively have vertically oriented plates 21 and 23 with curved upper edges 25 and plural threaded openings 27.

The side plates have multiple threaded holes so that the position of the nose pad may be adjusted upward and downward with respect to the plates and the cross-member, and rearward and forward with respect to the plates. The nose-engaging members 35 are supported on threaded rods 31, which have knobs 33 affixed to the outer ends of the threaded rods.

The nose-engaging members have threaded bushings 37 which are threaded on inner proximal ends of the threaded rods 31. The soft nose-engaging members 35 entirely close or restrict openings of the nostrils of a user. Cushions 41 are secured inside of the inner extension 13, and similar cushions are secured inside of the plates 21 and 23. The straps 43 are provided with complementary hook-type fasteners 45 and loop-type fasteners 47 to adjust the straps to the head of a user.

As shown in FIG. 4, the fastener 51 is inserted from the inside of the extension 13, through the opening 53 in the channel 17, and through the opening 55 in the extension bar 15. The head 57 of the fastener rides in a groove in the rear face of the extension member 15. Loosening nut 19 permits the extension members to relatively slide to precisely position the plates 21 and 23 on the sides of a nose of a user. Then the nut 19 is tightened and the fasteners 45 and 47 on straps 43 are engaged to hold the device on the head of a user. Turning knobs 33 compress the nose-engaging pads 35 against the nostrils for selectively closing the nostrils.

FIG. 4 shows the plates 21 and 23 reversed so that the left plate has the extension bar 15 and the right plate has the groove 17 in the extension 13. That is simply to show that the plates may be molded in either form.

Once the device has been adjusted for a particular user, it is only necessary to open the fasteners 45 and 47 to remove the device from a user's head, and when using the device to replace the device on a user's head and close the fasteners 45 and 47. No further adjustment is necessary. For comfort or to change the pressure on each nostril, the knobs 33 may be turned.

Initially in selecting the most comfortable and effective position, the threaded bushings are removed from the inner proximal ends 39 of the rods 31, and the threaded rods 31 are replaced in different threaded holes 27 by turning the knobs 33 which are fixed to the ends of the threaded rods. Then the bushings 37 may be threaded on the inner ends 39 of the rods, securing the nose pads 35 in position.

While the invention has been described with reference to specific embodiments, modifications and variations of the invention may be constructed without departing from the scope of the invention, which is defined in the following claims.

I claim:

1. An apparatus, comprising a frame having first and second side plates, first and second central extensions extending respectively from the first and second side plates, the first and second extensions having slides for relatively sliding the extensions, and having a clamp connected to the extensions for clamping the extensions in a selected interrelationship of the slides, first and second nose-engaging pads for engaging and compressing sides of a nose with the pads, and a strap connected to the plates for holding the plates on the face of a user.

2. The apparatus of claim 1, further comprising first and second rods respectively mounted in the first and second plates, the first and second rods having respective first and second proximal ends extending inward from the plates toward each other, and first and second nose-engaging pads are connected to the rods.

3. The apparatus of claim 2, wherein the plates have cushions spaced from the nose-engaging pads for resting against a face of a user, and wherein the cushions are located along inner surfaces of the plates and along rearward and lower edges of the inner surfaces.

4. The apparatus of claim 1, further comprising cushions on one of the extensions for engaging a facial area of a user above an upper lip of the user and beneath a nose of the user.

5. The apparatus of claim 1, wherein the slides comprise a curved outward opening channel formed in a first inner extension connected to a first plate, wherein the second extension is formed as a curved bar for sliding in the outward facing channel, and wherein the cushions are mounted around a rearward facing portion of the forward opening channel.

6. The apparatus of claim 1, wherein the slides comprise a curved outward opening channel formed in a first inner extension connected to a first plate, and wherein the second extension is formed as a curved bar for sliding in the outward facing channel.

7. The apparatus of claim 6, further comprising an elongated opening extending along the base of the channel and a recess in a rear face of the first extension, wherein the second extension comprises a hole extending through the extension, and wherein the clamp further comprises a fastener extending through the hole with a head of the fastener in the recess.

8. The apparatus of claim 7, wherein the clamp further comprises a clamping nut engaging the fastener in front of the second extension.

9. The apparatus of claim 2, wherein the first and second plates have multiple openings for receiving the rods.

10. The apparatus of claim 9, wherein the multiple openings are threaded and wherein the rods have complementary threads, and wherein the rods have knobs fixed on outer ends thereof for turning the rods and the pads connected to the proximal ends of the rods inward and outward according to the turning of the rods in the holes, and wherein the multiple holes comprise precise positioning of the rods for precise positioning of the pads on sides of the nose of the user.

11. The apparatus of claim 10, wherein the pads have threaded bushings for receiving proximal ends of the threaded rods and for mounting the pads on the threaded proximal ends of the rods for removing the pads from the proximal ends and turning the rods out of the holes for repositioning the rods in other holes before re-securing the threaded the bushings and pads to proximal ends of the rods for correctly aligning the pads with surfaces of the nose of the user.

12. The apparatus of claim 1, wherein the strap comprises first and second strap sections, the first strap section connected to the first plate having an outward facing hook-type fastener strip, and the second strap fastened to the second plate and having at an outer end thereof an inward facing loop-type fastener strip complementary to the hook-type fastener strip.

13. A device comprises a frame having first and second plates for positioning on a face along opposite sides of a nose, the plates further comprising first and second extensions extending forwardly and inwardly and contacting a face of a user beneath a nose and above an upper lip, rods extending inward from the plates, and nose-engaging pads mounted on inward ends of the rods, a strap connecting the plates and extending rearwardly around a head of a user, the strap having first and second sections with ends having hook and loop complementary fasteners for adjusting the strap to fit a head of a user, and holding the strap.

14. The apparatus of claim 13, wherein the extensions have a curved channel and a curved bar which slides within the curved channel for adjusting position between the plates.

15. The apparatus of claim 14, further comprising a threaded clamp having an enlarged head mounted in an elongated recess at a rear of the channel, and having a threaded shaft extending through an elongated opening in the channel and through an opening in the curved bar which slides within the channel, and a fastener nut threaded on an outer end of the threaded shaft for clamping the curved bar and curved channel in selected positions.

16. The apparatus of claim 13, wherein inward facing surfaces of the plates have cushions along rear edge and bottom edge portions, and one of the extensions having cushions along edges for contacting a user's face.

17. The apparatus of claim 13, wherein the plates have multiple threaded openings in which the rods may be selectively received.

18. A method of restricting nasal openings, comprising unscrewing threaded bushings connected to nose pad holders from inner distal ends of rods, unscrewing the rods from threaded openings in plates using knobs at distal ends of the rods, screwing the rods into other threaded openings in the plates, screwing the threaded bushings on the pad holders onto inner end of the rods, supporting the plates on extensions extending between a nose and upper lip of the user and securing the device with straps extending rearward from the plates around a back of a head of a user, turning the knobs and the rods inward and compressing sides of a nose to close the nasal passageways or until the nasal passageways are restricted sufficiently to control vibrations of the uvula and soft palate.

\* \* \* \* \*